United States Patent [19]

Wolf et al.

[11] Patent Number: 4,946,949
[45] Date of Patent: Aug. 7, 1990

[54] POLYMERIZABLE AROMATIC-AZO-ALIPHATIC COMPOUNDS AND POLYMERS MADE THEREFROM

[75] Inventors: Richard A. Wolf; Alan E. Platt, both of Midland, Mich.

[73] Assignee: The Dow Chemical Company, Midland, Mich.

[21] Appl. No.: 211,194

[22] Filed: Jun. 24, 1988

[51] Int. Cl.$^5$ .................. C07C 107/52; C07C 107/04; C08G 63/00
[52] U.S. Cl. .................................... 534/885; 524/190
[58] Field of Search ........................................ 534/885

[56] References Cited

U.S. PATENT DOCUMENTS

| | | | |
|---|---|---|---|
| 3,649,614 | 3/1972 | Sheppard et al. | 534/838 X |
| 3,763,129 | 10/1973 | Sheppard et al. | 534/838 X |
| 3,868,359 | 2/1975 | Sheppard et al. | 534/838 X |
| 3,937,761 | 2/1976 | MacLeay et al. | 534/838 X |
| 3,957,750 | 5/1976 | MacLeay et al. | 534/838 X |
| 3,987,024 | 10/1976 | MacLeay et al. | 534/838 X |
| 4,094,868 | 6/1978 | Chandalia et al. | 534/838 X |

OTHER PUBLICATIONS

Porter et al., *Photorearrangement of an Unsymmetric Azo-Compound*, 1971 J. Chem. Soc. 1575 (1971).
Gründemann, *A New Method for the Preparation of Unsaturated Azo Compounds*, 8 Angew. Chem. Intern'l Ed. Eng. 459 (1969).
Engel et al., *Thermolysis of Acyclic Azoalkanes: Simultaneous or Stepwise C–N Homolysis*, 105 J. Am. Chem. Soc. 6849, 6850 (1983).
Porter et al., *cis-Intermediates in Azo-Compound Photolysis*, 1973 J. Chem. Soc. 263, 264 (1973).
Brodka et al., *Darstellung neuer Azo-alkene und Derivate, insbesondere Additionsprodukte CH-acider Verbindungen*, 745 Liebigs Ann. chem. 193, 195 (1971).
Kerber et al., *Synthese und Charakterisierung von Copolymeren aus Azo-Initiatoren und Styrol*, 177 Makromol. Chem., 1357-1371 (1976).
Kerber et al., *Pfropfung und Vernetzung mittels Azogruppen enthaltender Copolymerer*, 6, 178, Makromol. Chem. 1833-1839 (1977).
Kerber et al., *Uber die Copolymerization Von (3-Vinylphenylazo)-methylmalonodinitril mit Styrol*, 179, Makromol. Chem. 1803-1814 (1978).
Nuyken et al., *Radical Efficiency and Ionic Reactions of some Unsymmetrical Azo compounds*, 184, Makromol. Chem., 2251-2259 (1983).
Oppenheimer et al., *The Synthesis of Blockcopolymers by Radical Polymerization*, 98, Die Angewandte Makromolekulare Chemie, 167-184, (1981).
Furukawa et al., *Preparation of Block Copolymers with Macro-Azonitrile as an Initiator*, Angewandte Makromolekulare Chemie 1, 92-104 (1967).
Smith, *The Thermal Decomposition of Azonitrile Polymers*, Die Makromolekulare Chemie 103, 301-303 (1967).
Fowler, *A New Synthesis of Unsymmetrical Azo Compounds*, J. Org. Chem., vol. 37, No. 3, 1972.
Bellamy et al., *Studies on the Possible Interconversion of Phenylhydrazones and Phenylazoalkanes*, J. Chem. Soc. (London) 2788 (1965).
O'Connor, *Tautomerism in Phenylhydrazones*, J. Org. Chem. 4375 (1961).
Curtin et al., *Reaction of Diarylzinc Reagents with Aryldiazonium Salts.*
*Direct Formation of cis-Azo Compounds*, 26 J. Org. Chem. 1764 (1961).
Curtin et al., *Reaction of Organometallic Compounds with Diazonium Salts.*
*Synthesis of Arylazoalkanes*, 21 J. Org. Chem. 1221 (1956).
Kerber et al., *Substituenteneinfluss auf die Kinetik des thermischen Zerfalls von Unsymmetrischen Azonitrilen und Azodinitrilen*, 164 Die Makromolekulare Chemie 164, 183-202 (1973).
Hinz et al., *Zur Frage des Einstufigen oder Mehrstufigen Verlaufs der Azoankanthermolyse*, 173 Tetrahedron Lett. 1975 (1973).
Kerber et al., *Der asynchrone Zerfall einiger Arylazomalodinitrile*, Die Makromolekulare Chemie 170, 155-164 (1973).
Kerber et al., *Azoinitiatoren*, (9) *Synthese und Pfropfung azogruppenhaltiger Polycarbonate*, 180 Makromolecular Chem. 609 (1979).

*Primary Examiner*—Floyd D. Higel

[57] ABSTRACT

Compounds which comprise an azo group linking an aliphatic group to an olefin-bearing aromatic group, for example t-butylazostyrene, can be polymerized at temperatures of 130° C. or more without causing substantial thermal decomposition of the azo group. The compounds and their polymers may be stored indefinitely at ambient temperatures. The azo group in the polymer will decompose at temperatures in excess of 240° C. to become a free radical initiator or cross-linking agent.

13 Claims, No Drawings

POLYMERIZABLE AROMATIC-AZO-ALIPHATIC COMPOUNDS AND POLYMERS MADE THEREFROM

BACKGROUND OF THE INVENTION

The present invention pertains to the field of polymers containing active azo moieties and monomers for making those polymers.

Graft and block copolymers are copolymers wherein specific areas of the polymer contain different combinations of mer units. For instance, in a graft polymer a polymer backbone comprising one combination of mer units is attached to polymer branches which consist of a different combination of mer units. Such graft copolymers are conveniently made by forming a polymer backbone with initiator sites that may be used to initiate polymerization in a different monomer composition. Organic azo compounds are known to initiate free radicals at the site of the azo group through thermally, photolytically and chemically induced decomposition of the azo group.

Kerber et al. demonstrated that $\alpha$, $\alpha$-dicyanoethylazostyrene could be copolymerized with styrene at temperatures of about 0° C. to 60 C. to form a polystyrene backbone with pendant dicyanoethylazo moieties. The azo group could subsequently be decomposed by temperatures of about 70° C. or more to initiate polymerization in vinylic monomers. Kerber et al., *Synthese und Charakterisierung von Copolymeren aus Azo-initiatoren und Styrol*, 177 Makromolecular Chem. 1357-1371 (1976); Kerber et al., *Propfung und Vernetzung mittels Azogruppen enthaltender Copolymerer*, 6, 178 Makromolecular Chem. 1833 (1977); Kerber et al., *Uber die Copolymerisation von (3-Vinylphenylazo)-methylmalonodinitril mit Styrol*, 179 Makromolecular Chem. 1803 (1978); Kerber et al., *Azoinitiatoren, (9) Synthese und Profung azogruppenhaltiger Polycarbonate*, 180 Makromolecular Chem. 609 (1979).

The cyanoethyl-azo-styrene monomers and polymers of Kerber et al. share several problems which decrease their commercial utility. The azo group in the Kerber monomers and polymers is highly temperature sensitive and decomposes swiftly even at low temperatures of about 70° C. The polymer is unstable for extended shelf-life. Furthermore, the polymer cannot be formed or purified by processes which proceed at temperatures in excess of 70° C.

What is needed is a polymer containing pendant azo moieties which can be produced and processed at relatively high temperatures, which can be stored indefinitely at room temperature, and which can be subjected to sufficient heat later to cause thermal decomposition of the azo group.

SUMMARY OF THE INVENTION

One aspect of the present invention is an azo compound comprising:
(1) an azo group consisting of a first nitrogen atom and a second nitrogen atom:
(2) an aromatic moiety bonded to the first nitrogen atom of said azo group, said aromatic moiety having a polymerizable olefin substituent: and
(3) an aliphatic hydrocarbyl moiety bonded to the second nitrogen atom of said azo group said aromatic moiety and aliphatic hydrocarbyl moiety being chosen such that said azo group has a half-life of at least about 6 hours at about 130° C. and a half-life of no more than about 20 minutes at 375° C.

Another aspect of the present invention is a polymer comprising:
(1) backbone having a plurality of pendant aromatic moieties:
(2) a plurality of azo groups, each consisting of a first nitrogen atom and a nitrogen atom and each bonded by said first nitrogen atom to one of the pendant aromatic moieties; and
(3) an aliphatic hydrocarbyl moiety bonded to the second nitrogen atom of each said azo group said pendant aromatic moieties and aliphatic hydrocarbyl moieties being chosen such that said azo group has a half-life of at least about 6 hours at about 130° C. and a half-life of no more than about 20 minutes at 375° C.

Azo compounds of the present invention can be polymerized through polymerization of the olefin substituent to form polymers of the present invention having azo groups attached to pendant aromatic moieties. Polymers can be subjected to elevated temperatures to thermally decompose the azo groups. Thermal decomposition of the azo group yields nitrogen which can foam the polymer. It also yields free radicals sited on the pendant aromatic moieties which can initiate cross-linking within the polymer or polymerization with another monomer to form a graft copolymer.

DETAILED DESCRIPTION OF THE INVENTION

Compounds of the Present Invention

Compounds of the present invention comprise an azo group which consists of a first and a second nitrogen atom. The compounds may bear a plurality of azo groups per molecule, but each molecule preferably has only one azo group.

Compounds of the present invention comprise an aromatic moiety that is bonded to the first nitrogen atom of said azo group and has at least one substituent which has a polymerizable olefin moiety. The aromatic moiety may be heterocyclic but is preferably carbocyclic and more preferably hydrocarbyl. Although the size of the aromatic moiety is not critical to the invention, the aromatic moiety preferably comprises no more than about 10 carbon atoms: more preferably, no more than about 6 carbon atoms. The aromatic moiety may be, for example, a pyridinylene, furanylene or thiophenylene group or an arylene such as phenylene or naphthylene. Preferred examples are phenylene or naphthylene groups and the most preferred example is a phenylene group.

The aromatic group has a polymerizable olefin substituent. Its size is not critical as long as the size does not interfere with polymerization. The olefin substituent preferably comprises no more than about 6 carbon atoms: more preferably, no more than about 3 carbon atoms It is most preferably a vinyl moiety. The olefin substituent is preferably meta to the azo group. Preferred examples of the olefin substituent are vinyl, isopropenyl, vinylidene, n-propenyl and n-butenyl groups.

Practical considerations such as steric hindrance limit the presence of other substituents on the aromatic moiety. Other substituents should not interfere with polymerization of the olefin moiety due to steric or other effects. Substituents are preferably halo or hydrocarbyl: highly preferably, chloro, bromo or lower alkyl (no more than about 4 carbons): and more highly preferably, chloro, methyl or ethyl. Most preferably, the aromatic moiety contains no substituents other than the olefin substituent. In their most preferred embodiments, the aromatic moiety and olefin substituent are combined to form a meta-styryl moiety.

If the aromatic moiety has other substituents, they are preferably located ortho to the azo group. Preferred substituents ortho to the azo group may cause the azo group to begin rapid thermal decomposition at a temperature about 10° C. to about 25° C. lower than the thermal decomposition temperature of an unsubstituted compound. Substituents on the aromatic moiety are more preferably located para to the olefin substituent.

The second nitrogen atom of the azo group is bonded to an aliphatic hydrocarbyl moiety. The aliphatic hydrocarbyl moiety may have substituents containing aromatic moieties or heteroatoms located no closer to the azo group than the γ carbon. (For the purposes of this discussion, the carbon atom bonded to the azo group is the c carbon, carbon atoms adjacent to the α carbon are the β carbons, and carbon atoms adjacent to the β carbons are the γ carbons.) The aliphatic hydrocarbyl moiety preferably has no substituents containing aromatic moieties or heteroatoms. It more preferably is saturated at the α and β carbons. It most preferably is an unsubstituted alkyl group. Aliphatic hydrocarbyl moieties are preferably secondary or tertiary and more preferably tertiary at the α carbon.

The aliphatic hydrocarbyl moiety preferably comprises no more than about 12 carbon atoms, more preferably no more than about 8 carbon atoms, and most preferably no more than about 6 carbon atoms. The aliphatic hydrocarbyl moiety preferably comprise no fewer than about 3 carbon atoms, more preferably no fewer than about 4 carbon atoms. Larger groups may cause the azo moiety to decompose at somewhat lower temperatures. The aliphatic hydrocarbyl moiety may be, for example, a secondary or tertiary butyl, pentyl, hexyl, heptyl or octyl group, a cyclohexyl group, a 1-methylcyclohexyl group, or an isomer or homolog of one of those groups. A highly preferred example is a t-butyl group.

Azo compounds of the present invention are preferably represented by the formula:

Q—Ar—N=N—R wherein Q is a polymerizable olefin moiety, Ar is an aromatic moiety and R is an aliphatic hydrocarbyl moiety as those groups are previously described. Azo compounds of the present invention are more preferably represented by the formula:

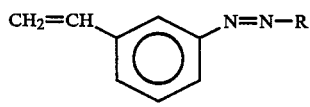

wherein R is an aliphatic hydrocarbyl moiety as that term is previously defined.

Azo compounds of the present invention can be prepared by the reaction of an an organometallic compound with olefin-bearing aromatic diazonium salt, which is prepared from an olefin bearing aromatic amine. First, the olefin-bearing aromatic amine, such as aminostyrene, is prepared by reaction of the corresponding aromatic nitro compound with stannous chloride in the presence of acid, such as concentrated hydrochloric acid, and alcohol, such as ethanol, at ambient temperatures or with heating. Conditions are described in Bigge et al., *Palladium-Catalyzed Coupling Reactions of Uracil Nucleosides and Nucleotides,* 102 J. Am. Chem Soc. 2033, 2036 (1980), which is incorporated herein by reference. The aromatic moiety and olefin substituent of the nitro compound and amine become the aromatic moiety (Ar) and the olefin substituent (Q) of the final product compound.

Second, the amine group is oxidized to form a corresponding diazonium salt by an oxidizing agent, such as sodium nitrite, which is capable of oxidizing the amine to a diazonium moiety in the presence of a non-nucleophilic agent such as fluoboric acid or antimony hexafluoride in order that the diazonium moiety not be displaced from the anion.

Third, the resulting diazonium ion is reacted with an appropriate organometallic compound. The organometallic compound is, for example, a compound of the formula R-ZnCl, R-MgCl, R-MgBr, R-MgI or R-ZnBr, wherein R corresponds to the aliphatic hydrocarbyl moiety desired in the azo compound. The reaction of the diazonium ion with the organometallic compound typically takes place in a suitable anhydrous solvent, such as diethylether, tetrahydrofuran, dioxane, hexane, pentane or ether/alkane mixtures, under subambient temperatures in order to maintain the temperature below the decomposition temperature of the diazonium ion. Isolation of the product is performed using techniques such as vacuum distillation or column chromatography. Conditions and parameters for the synthesis from amine to azo compound are described by Curtin et al., *Reaction of Organometallic Compounds with Diazonium Salts. Synthesis of Arylazoalkanes,* 21 J. Org. Chem. 1221-25 (1956), which is incorporated herein by reference.

Unsubstituted and ortho-substituted azo compounds useful in this invention are also prepared by reacting a tertiary alkyl primary amine compound with an aromatic compound having an olefin substituent and an isocyanate substituent. The reaction provides an aryl-/alkyl urea compound, which is oxidized to provide the desired azo compound. The procedure is described in Fowler, *A New Synthesis of Unsymmetrical Azo Compounds,* 37 J. Org. Chem. 510-11 (1972), which is incorporated herein by reference.

Typically, the isocyanate-substituted aromatic compound and tertiary alkyl primary amine compound are contacted in a suitable anhydrous solvent such as pentane, heptane, hexane, benzene, toluene, chloroform, carbon tetrachloride or methylene chloride. If desired, a catalyst or initiator such as a hindered tertiary amine can be employed. The resulting urea compound is contacted with an oxidizing agent such as sodium hypochlorite, t-butylhypochlorite, potassium perchlorate, sodium chlorite, calcium hypochlorite, or sodium hypobromite. Sufficient oxidizing agent is employed in order to oxidize the urea functionality to provide the desired azo functionality. Most preferably, the oxidation of the urea compound is performed in a basic environment using sodium hypochlorite. The product is isolated by known techniques such as vacuum distillation or column chromatography.

The azo group in compounds of the present invention is substantially stable with respect to thermal decomposition under low and moderate temperatures. The group is considered substantially stable if its half-life is at least about 6 hours: preferably, at least about 12 hours; and more preferably, at least about 24 hours under the conditions set forth herein. Compounds of the present invention are substantially stable at about 130° C.; preferably, at about 180° C.; and more preferably, at about 240° C. The half-life is most preferably months at room temperature and days at about 130° C. to 180° C.

POLYMERS OF THE PRESENT INVENTION

Because of their stability in the absence of light, compounds of the present invention can readily be incorporated into polymers by polymerization of the olefin moiety without causing substantial decomposition of the azo group. The polymers into which compounds of the present invention are incorporated are those which may contain styryl mer units. For instance, compounds of the present invention may be copolymerized with styrene, butadiene, acrylonitrile, methyl methacrylate or other known unsaturated monomers. Compounds of the present invention are preferably incorporated into polystyrene, styrene-acrylonitrile (SAN), styrene-butadiene (SB) or acrylonitrile-butadiene-styrene (ABS) polymers. More preferably, compounds of the present invention are copolymerized with styrene or made part of SAN polymers.

Since important utilities for polymer compositions of the present invention generally require thermal decomposition of the azo groups at such high temperatures, the polymer backbone formed by polymerization of the olefin moiety is preferably one which can withstand those temperatures without decomposing itself. Compounds of the present invention are preferably incorporated into polymer systems which can, for a short time, withstand temperatures up to about 275° C.; more preferably, up to about 300° C.: and most preferably, up to about 325° C.

The ratio of azo bearing monomers to other monomers used in making the polymer will depend to a great extent upon the desired use for the azo group. For instance, if the azo group is intended to initiate cross-linking or further polymerization, the proportion of azo bearing monomers will reflect the desired density of cross-linking or grafting of polymer. Compounds of the present invention preferably make up no more than about 10 percent of the monomers used to make the polymer: more preferably, no more than about 5 percent: and most preferably, no more than about 2 percent. Compounds of the present invention preferably make up at least about 0.01 percent of the monomers used to make the polymer: more preferably, at least about 0.1 percent: and most preferably, at least about 1 percent.

Polymerization may be accomplished by any method known for polymerizing styrene monomer, as long as the method does not require substantial exposure to temperatures at which the azo group is not substantially stable. For instance, the polymer may be formed in temperatures of up to about 240° C., more preferably up to about 180° C., as long as the polymer is not subjected to moderate light.

Conditions and methods for such polymerization are well-known to persons skilled in the art. For instance, the polymerization may be carried out by a free radical mechanism using initiators such as azo diisobutyronitrile (AIBN), peroxides, oxidation-reduction systems and the like. Polymerization is carried out by mixing the monomers and initiator in a reaction vessel and then subjecting the initiator to temperatures at which the initiator decomposes generating free radicals to initiate polymerization. Among known initiators, for instance, benzoyl peroxide will initiate polymerization at temperatures from about 55° C. to about 115° C., and AIBN will initiate polymerization at temperatures from about 70° C. to about 100° C. Polymerizations are described in Overberger, "Bulk Polymerization with Peroxide Catalyst", 1 *Macromolecular Synthesis* 5 (1977 J. Moore ed.) and Ingram et al., "Expandable Polystyrene Beads", 1 *Macromolecular Synthesis* 349 (1977 J. Moore ed.), which are incorporated herein by reference.

Anionic mechanism polymerization can also be initiated by an organometallic compound such as n-butyllithium. The initiator is added under vacuum at a low temperature, such as about 0° C. to 30° C., to a purified mixture of monomer, a solvent such as benzene and an accelerant such as tetrahydrofuran. Such a reaction is fully described in Fetters et al., "Polystyrene with Predictable Molecular Weights and Uniform Molecular Weight Distributions", 1 *Macromolecular Synthesis* 463 (1977 J. Moore ed.), which is incorporated herein by reference.

Cationic method polymerization can be initiated by a known cationic initiator, such as stannic chloride. Stannic chloride is dried and dissolved in a solvent such as carbon tetrachloride in a concentration of about 2 percent by weight. The initiator is added to dried monomer in a solvent, such as carbon tetrachloride and nitrobenzene, under low temperatures such as about 0° C. Such a polymerization is described fully in Overberger, "Solution Polymerization with Cationic Catalysis", 1 *Macromolecular Synthesis* 6 (1977 J. Moore ed.), which is incorporated herein by reference.

If the polymerizable olefin moiety is remote from an activating group such as the aromatic group, then it will tend to resist free radical polymerization in a manner familiar to persons skilled in the art. In such cases, polymerization using a Ziegler-Natta system is appropriate. Compounds of the present invention may also be polymerized by known methods of emulsion polymerization, suspension polymerization, solution polymerization or thermally initiated polymerization.

Polymer compositions of the present invention comprise a polymer backbone having pendant aromatic moieties. The pendant aromatic moieties have the same limitations and preferred embodiments set out previously to describe the aromatic moieties in compounds of the present invention. At least some of the pendant aromatic moieties are bonded to the first nitrogen of an azo group. The azo group is preferably located on the pendant aromatic moiety meta to the polymer backbone. The second nitrogen of each azo group is bonded to an aliphatic hydrocarbyl moiety which has the same limitations and preferred embodiments set out previously to describe the aliphatic hydrocarbyl moieties in compounds of the present invention.

Polymers of the present invention are preferably represented by the formula:

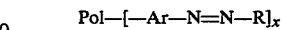

wherein
  Pol represents the polymer backbone;
  Ar represents a pendant aromatic moiety:
  R represents an aliphatic hydrocarbyl moiety; and
  x represents a number of pendant azo bearing moieties greater than 1.

Pol, Ar and R all have the limitations and preferred embodiments previously used to describe the polymer, aromatic moieties and aliphatic hydrocarbyl moieties. Polymers of the present invention are preferably represented by the formula:

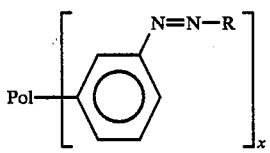

wherein Pol, R and x have the meanings previously given.

Mer units having pendant azo moieties preferably make up no more than about 10 percent of the mer units in the polymer: more preferably, no more than about 5 percent; and most preferably, no more than about 2 percent. Mer units having pendant azo moieties preferably make up at least about 0.01 percent of the mer units in the polymer: more preferably, at least about 0.1 percent: and most preferably, at least about 1 percent.

The azo groups in polymers of the present invention preferably have a half-life of months with respect to thermal decomposition of the azo moiety at room temperature. The azo groups in polymers of the present invention are substantially stable at about 130° C.; preferably at about 180° C.; and more preferably at about 240° C.

Compounds and polymers of the present invention preferably undergo substantial decomposition of the azo group at about 350° C.; more preferably at about 325° C.; and most preferably at about 300° C. Substantial decomposition means that the azo group has a half-life of no more than about 20 minutes: more preferably, no more than about 5 minutes: more highly preferably, no more than about 2 minutes: and most preferably, no more than about 1 minute. Ordinarily, the azo group in a compound or polymer of the present invention decomposes faster with a shorter half-life at higher temperatures within the range at which it decomposes.

Polymers of the present invention may be used as high temperature initiators. They may serve as the central backbone for forming graft copolymers. Furthermore, the azo group may serve as a cross-linking agent in the polymer or may serve as a source of nitrogen gas for foaming the polymer.

ILLUSTRATIVE EXAMPLES

The following examples are for illustrative purposes only and are not to be taken as restricting the scope of either the claims or the specification. Unless otherwise specified, all parts and percentages are by weight.

Example 1

Synthesis of m-(t-butylazo)-styrene m-Nitrostyrene (8.70 g) is converted to m-aminostyrene by the method of C. F. Bigge et al., *Palladium-Catalyzed Coupling Reactions of Uracil Nucleosides and Nucleotides*, 102 J. Am. Chem Soc. 2033, 2036 (1980). The m-aminostyrene is added to 24.5 g. of 48 percent aqueous fluoboric acid and 27 ml of water in a 100-ml round-bottom flask with a stir bar in an ice water bath. Sodium nitrite (4.31 g) dissolved in 9 ml of water is added slowly with stirring. The resulting thick precipitate is permitted to digest for one hour in the ice water bath cooling and is collected by suction filtration. The precipitate is washed with successive ice-cold washes of 45 ml of 5 percent aqueous fluoboric acid, 40 ml of methanol, and 50 ml of diethylether. The precipitate is dried in a vacuum desiccator at high vacuum for 2.5 hours. The yield is about 7.71 g of m-styryldiazonium fluoborate.

Zinc chloride (10.41 g) is melted in a 250-ml round-bottom flask under vacuum of 1 ml of mercury to remove water. After cooling, 100 ml of anhydrous diethylether is added to the flask. A rubber septum, a reflux condenser and a drying tube are added to the flask. 2N t-butyl magnesium chloride (21 ml) in diethylether is added with stirring and stirred for about 55 minutes.

m-Styryldiazonium fluoborate (7.71 g) and 80 ml of anhydrous diethylether are added to a 500-ml round-bottom flask. The mixture containing t-butyl zinc chloride is added by pushing over through a Teflon ® tube using nitrogen gas. The resulting suspension is stirred with ice water cooling for about 40 minutes and then is stirred at ambient temperature for about 40 minutes. The reaction mixture is rechilled and a mixture of 50 ml of saturated aqueous ammonium chloride and 40 ml of water is added. The resulting mixture is stirred with cooling for 30 minutes. Ether and water layers are separated, and solids are washed with additional ether. The water layer is washed with additional ether. The combined ether layer and washes are dried with anhydrous sodium sulfate and the ether is removed by vacuum.

The product is 4.33 g of a brown liquid. That liquid is purified by passing through a column of 110 g of neutral alumina using pentane as an eluent. After removal of the pentane, 2.97 g of the title compound are recovered as a light yellow oil.

Example 2

Copolymerization of m-(t-butylazo)-styrene and styrene monomer

A solution of 1.00 percent by weight m-(t-butylazo)-styrene in styrene monomer is heated for 14 hours at 130° C. in a vacuum ampoule. Thereafter, the ampoule is opened and heated for 1 hour at 210° C. and 10 mm Hg pressure to remove unreacted monomer. An m-(t-butylazo)-styrene/styrene copolymer is obtained in a 96.2 percent yield.

Example 3

Cross-linking of m-(t-butylazo)-styrene/styrene copolymer through thermal decomposition of azo group A copolymer is produced and devolatilized as shown in Example 2 (Sample A). Polymers are produced under similar polymerization and devolatilization conditions from styrene monomer alone (Sample B) and from a mixture of 1 percent t-butylazobenzene in styrene monomer (Sample C). All three samples are heated to 250° C. for 2.7 hours. The average molecular weight of each sample is determined by size exclusion chromatography. The high $M_w$ and $M_z$ for Sample A, as shown in Table I (terms defined in F. W. Billmeyer, *Textbook of Polymer Science* 76 (Interscience Publ. 1965)), demonstrate that substantial cross-linking has occurred in the copolymer. On the other hand, polystyrene alone (Sample B) and polystyrene mixed with the unpolymerizable t-butylazobenzene (Sample C) show less cross-linking and Sample C shows no more cross-linking than polystyrene alone.

TABLE I

| Reaction | % Conversion of Styrene Monomer | Molecular Weights × 10⁻³ | | |
|---|---|---|---|---|
| | | $M_n$ | $M_w$ | $M_z$ |
| A | 96.2 | 167 | 425 | 713 |
| B* | 96.8 | 167.5 | 349 | 545 |
| C* | 93.5 | 164 | 346 | 540 |

*not an example of the invention.

What is claimed is:

1. An azo compound comprising:
   (1) an azo group;
   (2) an aromatic moiety bonded to one nitrogen atom of said azo group, said aromatic moiety having a polymerizable olefin substituent; and
   (3) an aliphatic hydrocarbyl moiety bonded to the other nitrogen atom of said azo group
   wherein the olefin moiety comprises no more than about 6 carbon atoms; the aromatic moiety is a carbocyclic group with no more than about 10 carbon atoms; and the aliphatic hydrocarbyl moiety comprises no more than about 12 carbon atoms, said aromatic moiety and aliphatic hydrocarbyl moiety being chosen such that said azo group has a half-life of at least about 6 hours at about 130° C. and a half-life of no more than about 20 minutes at 375° C.

2. The compound of claim 1 wherein the azo group has a half-life of at least 12 hours with regard to thermal decomposition at about 130° C.

3. The compound of claim 2 wherein the azo group has a half-life of at least about 24 hours with respect to thermal decomposition at about 130° C.

4. The compound of claim 2 wherein the azo group has a half-life of at least about 12 hours with regard to thermal decomposition at about 180° C.

5. The compound of claim 2 wherein the azo group has a half-life of at least about 12 hours with regard to thermal decomposition at about 240° C.

6. The compound of claim 2 wherein the olefin moiety can be polymerized without causing substantial decomposition of the azo group.

7. The compound of claim 1 wherein the substituent on the aliphatic hydrocarbyl moiety is a secondary or tertiary butyl, pentyl, hexyl, heptyl or octyl group, a cyclohexyl group, a 1-methylcyclohexyl group, or an isomer or homolog of one of those groups.

8. The compound of claim 1 which is represented by the formula:

wherein Q is the polymerizable olefin moiety, Ar is the aromatic moiety and R is the aliphatic hydrocarbyl moiety.

9. The compound of claim 1 wherein the olefin moiety comprises no more than about 3 carbon atoms; the aromatic moiety is a phenylene ring; and the aliphatic hydrocarbyl moiety is secondary or tertiary at the α carbon and comprises no more than about 8 carbon atoms.

10. The compound of claim 9 wherein the olefin and aromatic moieties make up an unsubstituted meta-styryl moiety and the aliphatic hydrocarbyl moiety is a secondary or tertiary alkyl group with no more than about 6 carbon atoms.

11. The compound of claim 10 which complies with the formula:

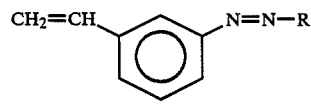

wherein R is the aliphatic hydrocarbyl moiety.

12. The compound of claim 10 wherein the aliphatic hydrocarbyl moiety is a tertiary butyl, pentyl, hexyl, heptyl, or octyl group, a cyclohexyl group, a 1-methylcyclohexyl group, or an isomer or homolog of one of those groups.

13. The compound of claim 12 wherein the compound is m-(t-butylazo)-styrene.

* * * * *

UNITED STATES PATENT AND TRADEMARK OFFICE
CERTIFICATE OF CORRECTION

PATENT NO. : 4,946,949

DATED : August 7, 1990

INVENTOR(S) : Richard A. Wolf and Alan E. Platt

It is certified that error appears in the above-identified patent and that said Letters Patent is hereby corrected as shown below:

Column 1, line 61, " nitrogen atom: " the punctuation should correctly read -- nitrogen atom; --.

Column 1, line 64, " substituent: " the punctuation should correctly read -- substituent; --.

Column 2, line 5, " (1) backbone " should correctly read -- (1) a polymer backbone --.

Column 2, line 6, " moieties: " the punctuation should correctly read -- moieties; --.

Column 2, line 8, " and a nitrogen atom " should correctly read -- and a second nitrogen atom --.

Column 2, line 47, " 10 carbon atoms: " the punctuation should correctly read -- 10 carbon atoms; --.

Column 2, line 58, " atoms: " the punctuation should correctly read -- atoms; --.

Column 2, line 59, " atoms It is " the punctuation should correctly read -- atoms. It is --.

Column 2, line 67, " hydrocarbyl: " the punctuation should correctly read -- hydrocarbyl; --.

UNITED STATES PATENT AND TRADEMARK OFFICE
CERTIFICATE OF CORRECTION

PATENT NO. : 4,946,949

DATED : August 7, 1990

INVENTOR(S) : Richard A. Wolf and Alan E. Platt

It is certified that error appears in the above-identified patent and that said Letters Patent is hereby corrected as shown below:

Column 3, line 1, " carbons): " the punctuation should correctly read -- carbons); --.

Column 3, line 21, " is the c carbon, " should correctly read -- is the α carbon --.

Column 3, line 34, " comprise no " should correctly read -- comprises no --.

Column 5, line 1, " 6 hours: " the punctuation should correctly read -- 6 hours; --.

Column 5, line 46, " polymer: " the punctuation should correctly read -- polymer; --.

Column 5, line 47, " cent: " the punctuation should correctly read -- cent; --.

Column 5, line 50, " polymer: " the punctuation should correctly read -- polymer; --.

Column 5, line 51, " percent: " the punctuation should correctly read -- percent; --.

Column 6, line 63, " aromatic moiety: " the punctuation should correctly read -- aromatic moiety; --.

UNITED STATES PATENT AND TRADEMARK OFFICE
CERTIFICATE OF CORRECTION

PATENT NO. : 4,946,949

DATED : August 7, 1990

INVENTOR(S) : Richard A. Wolf and Alan E. Platt

It is certified that error appears in the above-identified patent and that said Letters Patent is hereby corrected as shown below:

Column 7, line 16, " polymer: " the punctuation should correctly read -- polymer; --.

Column 7, line 20, " polymer: " the punctuation should correctly read -- polymer; --.

Column 7, line 21, " cent: " the punctuation should correctly read -- cent; --.

Column 7, line 34, " 20 minutes: " the punctuation should correctly read -- 20 minutes; --.

Column 7, line 35, " 5 minutes: " the punctuation should correctly read -- 5 minutes; --.

Column 7, line 36, " 2 minutes: " the punctuation should correctly read -- 2 minutes; --.

Signed and Sealed this

Twenty-first Day of April, 1992

Attest:

HARRY F. MANBECK, JR.

*Attesting Officer*       *Commissioner of Patents and Trademarks*